United States Patent [19]

Raykovitz et al.

[11] Patent Number: 4,944,993
[45] Date of Patent: Jul. 31, 1990

[54] TOUGHENED RUBBER BASED HOT MELT ADHESIVE COMPOSITIONS FOR DISPOSABLE APPLICATIONS

[75] Inventors: Gary Raykovitz, Flemington; Robert Schmidt, Great Meadows; Paul Puletti, Glen Gardner, all of N.J.

[73] Assignee: National Starch and Investment Holding Corporation, Wilmington, Del.

[21] Appl. No.: 233,181

[22] Filed: Aug. 17, 1988

[51] Int. Cl.$^5$ .............................................. B32B 27/00
[52] U.S. Cl. ..................................... 428/290; 428/343; 428/517; 428/521; 412/3; 281/29
[58] Field of Search ....................... 428/343, 290, 521; 281/29; 156/908; 412/3

[56] References Cited

U.S. PATENT DOCUMENTS

| | | | |
|---|---|---|---|
| 4,136,699 | 1/1979 | Collins et al. | 128/290 R |
| 4,411,954 | 10/1983 | Butch et al. | 428/343 |
| 4,526,577 | 7/1985 | Schmidt et al. | 604/366 |
| 4,578,302 | 3/1986 | Schmidt et al. | 428/110 |
| 4,660,858 | 4/1987 | Flanagan | 281/21 R |
| 4,704,110 | 11/1987 | Raykovitz et al. | 604/366 |
| 4,712,808 | 12/1987 | Beh-Forest et al. | 281/15 R |
| 4,722,650 | 2/1988 | Allen et al. | 412/3 |

*Primary Examiner*—Edith Buffalow
*Attorney, Agent, or Firm*—Ellen T. Dec; Edwin M. Szala

[57] ABSTRACT

Hot melt adhesive compositions suitable for disposable constructions are prepared from tackifying resins, oil diluent and a substantially radial styrene-butadiene block copolymer, the copolymer having a styrene content greater than about 35% by weight, a molulus at 300% elongation of at least 4.5 MPa and a solution viscosity less than about 1000 cps.

10 Claims, No Drawings

TOUGHENED RUBBER BASED HOT MELT ADHESIVE COMPOSITIONS FOR DISPOSABLE APPLICATIONS

Various block and multi-block thermoplastic rubbery copolymers comprising domains of polystyrene endblocks and rubbery butadiene midblocks are available. Depending on their specific physical characteristics, the various copolymers have been suggested for different end uses including some grades which are recommended for use in moldings or extrusions (e.g. footwear, automotive, hose, etc.) while other grades are recommended as adhesives, coatings or sealants.

We have now found that the use, in hot melt adhesive compositions for disposable applications, of a specific class of block copolymers normally recommended for the footwear industry provides adhesive compositions with a superior range of properties not heretofore achievable with conventionally employed adhesive grade block copolymers.

Thus, the present invention is directed to hot melt adhesive compositions suitable for disposable constructions comprising tackifying resins, oil diluent and a substantially radial styrene-butadiene block copolymer, the copolymer having a styrene content greater than about 35% by weight, a modulus at 300% elongation of at least 4.5 MPa and a solution viscosity less than about 1000 cps.

The resultant hot melt adhesives are useful in a wide variety of disposable applications. For example, adhesives characterized by relatively low viscosity and high tensile strength may be prepared for any number of disposable applications including construction and elastic attachment adhesives.

More specifically, the adhesives find use as construction adhesives in the multi-line or multi-dot (including spray) applications such as are described in U.S. Pat. No. 4,526,577. The adhesives are also very suitable for bonding of elastic to polyethylene and/or polypropylene, tissue and/or nonwoven substrates to form gathered waist, leg or sleeve bands in disposable articles such as described in U.S. Pat. Nos. 4,081,301; 4,259,220; 4,418,123; 4,543,099; 4,698,242, 4,699,941 and 4,419,494. Additionally, the combination of the toughened cohesive character of the adhesive coupled with its relatively low viscosity provides a superior adhesive for application to such substrates using conventional spray fiberization techniques wherein it is desirable to be able to spray the molten adhesive in a special pattern without disruption of the continuous adhesive filament, particularly at the edges of the spray pattern.

The block copolymers useful herein are comprised of styrene and butadiene blocks arranged in a substantially radial configuration and contain at least 35%, and generally up to about 50%, by weight of the styrene moiety. Of greater significance however, the copolymers selected should exhibit a modulus at 300% elongation of at least about 4.5 MPa and a solution viscosity less than about 1000 cps (25% in toluene at 23° C. using a Brookfield viscometer). These copolymers may be prepared using methods taught, for example, in U.S. Pat. Nos. 3,239,478; 3,427,269; 3,700,633; 3,753,936 and 3,932,327. Alternatively they are available from Shell Chemical Co. under the trademark Kraton DX1122 (37% styrene, modulus of 4.8 MPa, viscosity 670 cps) and from Eni Chem Americas (Agip USA Inc.) as Europrene SOL T 162LW/1 (40% styrene, modulus of 5.0 MPa, viscosity 750 cps) or SO1 T 162 LW/2 (40% styrene, modulus of 4.6 MPa, viscosity (640 cps). While the optimum amounts of the copolymer used in the adhesive will vary depending on the end use application, the copolymer will generally be present in the adhesive formulation at levels of about 10 to 40% by weight, preferably about 15 to 25% by weight.

The tackifying resins useful in the adhesive compositions can be hydrocarbon resins, hydrogenated hydrocarbon resins, synthetic polyterpenes, rosin esters, natural polyterpenes, and the like. More particularly, the useful tackifying resins include any compatible resins or mixtures thereof such as (1) natural and modified rosins such, for example, as gum rosin, wood rosin, tall oil rosin, distilled rosin, hydrogenated rosin, dimerized rosin, and polymerized rosin; (2) glycerol and pentaerythritol esters of natural and modified rosins, such, for example as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natural terpenes, e.g. styrene/terpene and alpha methyl styrene/terpene; (4) polyterpene resins having a softening point, as determined by ASTM method E28-58T, of from about 80° to 150° C.; the latter polyterpene resins generally resulting from the polymerization of terpene hydrocarbons, such as the bicyclic monoterpene known as pinene, in the presence of Friedel-Crafts catalysts at moderately low temperatures; also included are the hydrogenated polyterpene resins; (5) phenolic modified terpene resins and hydrogenated derivatives thereof such, for example, as the resin product resulting from the condensation, in an acidic medium, of a bicyclic terpene and a phenol; (6) aliphatic petroleum hydrocarbon resins having a Ball and Ring softening point of from about 70° to 135° C.; the latter resins resulting from the polymerization of monomers consisting of primarily of olefins and diolefins; also included are the hydrogenated aliphatic petroleum hydrocarbon resins; (7) aromatic petroleum hydrocarbon resins and the hydrogenated derivatives thereof; and (8) alicyclic petroleum hydrocarbon resins and the hydrogenated derivatives thereof. Mixtures of two or more of the above described tackifying resins may be required for some formulations. The tackifier is used in amounts of 20 to 65% by weight.

The remainder (up to about 60% by weight) of the hot melt adhesive comprises at least one oil diluent. Suitable plasticizing or extending oils include not only the usual plasticizing oils but also olefin oligomers and low molecular weight polymers as well as vegetable and animal oil and their derivatives. The petroleum derived oils which may be employed are relatively high boiling materials containing only a minor proportion of aromatic hydrocarbons (preferably less than 30% and, more particularly, less than 15% by weight of the oil). Alternatively, the oil may be totally non-aromatic. The oligomers may be polypropylenes, polybutenes, hydrogenated polyisoprene, hydrogenated polybutadiene, or the like having average molecular weights between about 350 and about 10,000.

Among the applicable stabilizers or antioxidants included herein are high molecular weight hindered phenols and multifunctional phenols such as sulfur and phosphorous-containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxy group. The presence of these sterically bulky substituted radicals in the vicinity of the hydroxyl group serves to retard its stretching frequency and, correspondingly, its reactivity; this steric hindrance thus providing the phenolic compound with its stabilizing properties. Representative hindered phenols include: 1,3,5-trimethyl 2,4,6-tris (3,5-di-tert-butyl-4-hydroxybenzyl)benzene; pentaerythrityl tetrakis-3(3,5-di-tert-butyl-4-hydroxyphenyl)propionate; n-octadecyl-3,5-di-tert-butyl-4-hydroxyphenol)-propionate; 4,4'-methylenebis (2,6-tert-butylphenol); 4,4'-thiobis (6-tert-butyl-o-cresol); 2,6-di-tertbutylphenol; 6-(4-hydroxy-phenoxy)-2,4-bis(n-octyl-thio)-1,3,5-triazine; di-n-octadecyl 3,5-di-tert-butyl-4-hydroxy-benzylphosphonate; 2-(n-octylthio)ethyl 3,5-di-tert-butyl—4-hydroxy-benzoate; and sorbitol hexa[3-(3,5-di-tert-butyl-4-hydroxyphenyl)-propionate]. The stabilizer is present in amounts of 0.1 to 4% by weight, preferably less than about 2%.

Optional additives may be incorporated into the hot melt compositions in order to modify certain properties thereof. Among these additives may be included colorants such as titanium dioxide; and fillers such as talc and clay, etc. as well as minor amounts (e.g. less than about 5%) of a petroleum derived wax.

These hot melt adhesive compositions may be formulated using techniques known in the art. An exemplary procedure involves placing approximately half of the total tackifying resin concentration in a jacketed mixing kettle, preferably in a jacketed heavy duty mixer of the Baker-Perkins or Day type, which is equipped with rotors and thereupon raising the temperature to a range of from about 250° to 350° F., the precise temperature utilized depending on the melting point of the particular tackifying resins. When the resin has melted, stirring is initiated and the block polymer and stabilizer are added together with any optional additives whose presence may be desired, the addition of the latter components being extended over a prolonged period in order to avoid the formation of lumps. Mixing and heating are continued until a smooth, homogeneous mass is obtained whereupon the remainder of the tackifying resin and the oil are thoroughly and uniformly admixed therewith. The resultant hot melt adhesives are generally produced with an oil in bulk form and packaged in release coated tube or boxes.

The resultant adhesives may be used in the assembly or construction of various disposable applications including, but not limited to, sanitary napkins, disposable diapers, hospital gowns, bed pads and the like. In particular, adhesives are useful for the assembly of disposable articles using multi-line construction techniques wherein at least one polyethylene or polypropylene substrate is bonded to at least one tissue, non-woven, polyethylene or polypropylene substrate. In addition, the adhesives are useful in the bonding of elastic to polyethylene, polypropylene or non-woven substrate so as, for example, to impart elongation resistant gathers thereto. The adhesive may also be utilized in less demanding disposable construction applications such as for end or perimeter sealing.

In the following illustrative examples all parts are given by weight and all temperatures in degrees Celsius unless otherwise noted.

EXAMPLE I

The following example illustrates the preparation of adhesives of the invention in formulations suitable for use in the disposables industry as discussed above.

In preparing the following samples, a heavy duty mixer which had been heated to 150° C. and which was equipped with a stirring paddle was charged with half of the tackifying resin. After melting of the resins, stirring was then initiated whereupon the block copolymers and the antioxidants were added slowly. Heating and stirring were continued until a homogeneous mass was obtained whereupon the remainder of the tackifying resin and the oil were admixed therewith. The molten mixture was then poured into a siliconized paper tube and cooled to room temperature.

Adhesives were prepared from the materials and amounts shown in Table I using the general procedure described above. Viscosity measurements were determined using a Brookfield viscometer (Spindle 27) at 325° F. The adhesives were subjected to the following tests to determine the heat resistance of the adhesive under a constant load and static stress and elevated temperature.

The adhesive was heated to 320° F. and a lamination of kraft paper was made using heated rollers. The adhesive thickness was 50 mil and the bonds having an adhesive area of one square inch. The bonds were aged overnight at 72° F. and 50% RH. The peel mode samples were then hung in a 105° F. oven using 300 gram/sq. inch weights. The time at which the bond failed was noted as was the mode of failure.

The tensile strength of the hot melt adhesive was determined on samples cast from the hot melts and molded in silicone rubber molds into the shape of dog bones. After cooling, the dog bone shaped specimens were removed from the mold and tested using an Instron Tensile Tester at a strain of 12 inches per minute. The force required to start to stretch the specimen is recorded as the "tensile yield", the maximum force attained is the "ultimate tensile".

TABLE I

| Sample | Polymer | Amount | Resin | Amount | Oil | Tensile Strength (MPa) Y | U | K/K (hrs) | Viscosity (cps) |
|---|---|---|---|---|---|---|---|---|---|
| 1 | DX1122X | 23 | Permalyn 305[1] | 59 | 18 | 0.06 | 1.17 | 3½ | 2975 |
| 2 | Sol T162 LW/1 | 23 | Permalyn 305 | 59 | 18 | 0.09 | 1.27 | 6½ | 3365 |
| 3 | Stereon 840A[2] | 23 | Permalyn 305 | 59 | 18 | 0.04 | 0.59 | 3½ | 2915 |
| 4 | DX1122X | 23 | Permalyn 305 | 57 | 20 | 0.05 | 1.16 | 5½ | 2950 |
| 5 | Firestone SR 7360[3] | 23 | Permalyn 305 | 57 | 20 | 0.04 | 0.86 | 2½ | 2525 |
| 6 | DX1122X | 21 | ECR 149B[4] | 60 | 19 | 0.05 | 1.17 | 2 | 2400 |
| 7 | Sol T162 LW/2 | 21 | ECR 149B | 60 | 19 | 0.07 | 1.27 | 2¾ | 2420 |
| 8 | Steteon 840A | 21 | ECR 149B | 60 | 19 | 0.04 | 0.62 | 3½ | 2470 |
| 9 | DX1122X | 15 | ECR 149A[5] ECR 149B | 30 30 | 25 | 0.03 | 0.82 | 1 | 760 |

TABLE I-continued

| Sample | Polymer | Amount | Resin | Amount | Oil | Tensile Strength (MPa) Y | U | K/K (hrs) | Viscosity (cps) |
|---|---|---|---|---|---|---|---|---|---|
| 10 | Stereon 840A | 21 | ECR 149A<br>ECR 149B | 30<br>30 | 19 | 0.05 | 0.72 | 5¼ | 2630 |
| 11 | Stereon 840A | 15 | ECR 149A<br>ECR 149B | 30<br>30 | 15 | 0.02 | 0.38 | 1⅝ | 685 |
| 12 | DX1122X | 21 | ECR 149A<br>ECR 149B | 30<br>30 | 19 | 0.07 | 1.3 | 7¼ | 3010 |
| 13 | DX1122X | 15 | Kristalex[6]<br>ECR 149B | 8<br>52 | 25 | 0.04 | 1.14 | 8¾ | 570 |
| 14 | Sol T162 LW/2 | 15 | Kristalex<br>ECR 149B | 8<br>52 | 25 | 0.04 | 1.22 | 6¼ | 805 |
| 15 | Firestone SR 7360 | 15 | Kristalex<br>ECR 149B | 8<br>52 | 25 | 0.03 | 0.73 | 3¼ | 765 |
| 16 | Stereon 840A | 15 | Kristalex<br>ECR 149B | 8<br>52 | 25 | 0.03 | 0.59 | 2¼ | 690 |
| 17 | DX1122X | 15 | Kristalex<br>ECR 149A | 8<br>52 | 25 | 0.06 | 1.24 | 25 | 1025 |
| 18 | DX1122X | 21 | M 105[7] | 60 | 19 | .06 | 1.19 | 16 | 2310 |
| 19 | SOL T162 LW/2 | 21 | M 105 | 60 | 19 | .08 | 1.39 | 16 | 2320 |
| 20 | Stereon 840A | 21 | M 105 | 60 | 19 | .04 | 0.83 | 4½ | 2450 |
| 21 | Stereon 840A | 21 | Res D2105[8] | 60 | 19 | .05 | 0.91 | 20½ | 2470 |
| 22 | Stereon 840A | 22.5 | Res D2105 | 60 | 17.5 | .06 | 1.06 | 40 | 2950 |
| 23 | SOL T168 | 22.5 | Res D2105 | 60 | 17.5 | .06 | 1.32 | 82 | 3535 |
| 24 | SOL T168 | 18 | Res D2105 | 60 | 22 | .02 | 0.85 | 4½ | 1390 |
| 25 | DX1122X | 18 | Res D2105 | 60 | 22 | .04 | 1.14 | 32½ | 935 |
| 26 | DX1122X | 15 | Res D2105 | 60 | 22*[9] | .03 | 0.98 | 8 | 600 |

[1]Permalyn 305 is a pentaerythritol ester of rosin from Hercules
[2]Stereon 840A is a styrene butadiene multi-block copolymer containing 43% styrene, having a modulus of 2.4 MPa and a viscosity of 650 cps. from Firestone
[3]Firestone SR 7360 is a styrene-butadiene polymer containing 43% styrene, having a modulus at 30% elongation of 3.7 MPa and a viscosity of 990 cps.
[4]ECR 149B is an aliphatic/aromatic $C_5/C_9$ resin from Exxon (95° C.)
[5]ECR 149A is an aliphatic/aromatic $C_5/C_9$ resin from Exxon (softening pt. 105° C.)
[6]Kristalex 5140 is an alpha methyl styrene resin from Hercules (140° C.)
[7]M 105 is a styrenated terpene resin from Reichhold
[8]Res D2105 is a styrenated terpene resin from Hercules
[9]Also contained 3 parts ECR 143H, a liquid aliphatic tackifying resin available from Exxon The testing results of Samples 1-8 show significantly higher ultimate tensile strength of the adhesives of the present invention when contrasted with presently commercially utilized adhesive compositions containing similar amounts of raw materials.

Sample 9 shows that it is possible to use less polymer to obtain a lower viscosity adhesive without sacrifice of tensile strength. (Compare to Sample 11 prepared with 15 parts Stereon). Note however the product did suffer with respect to Kraft/Kraft Heat Resistance Values and hence would not be readily useful for certain end use applications where stringent heat resistance values are required.

Samples 12, 13 and 14 show results similar to those of Sample 9, additionally overcoming the deficiency of Sample 9 with respect to heat resistance by use of a different tackifier.

Sample 17 shows a further formulation according to the invention using a different tackifying system. Note, in particular, the high heat resistance value.

Samples 18, through 26 again show the improved heat resistance and ultimate tensile strength achieved using adhesive compositions of the invention (e.g. Samples 18, 19, 25 and 26) as contrasted to conventionally employed Stereon or Sol T168 containing adhesive systems. Samples 24, 25 and 26 also show that lower levels of the Kraton D1122X may be used to obtain lower viscosity products without sacrifice to the tensile strength.

All of samples 1-26, on testing, gave entirely cohesive modes of failure in the Kraft to Kraft heat resistance test, i.e., adhesive residue was observed on both substrates after bond failure. This mode of failure is most desired since it indicates excellent wetting of both substrates.

EXAMPLE II

This example illustrates the unsuitability of a product marketed by Eni Chem Americas as Sol T162 (styrene content 40%; modulus 5.0, MPa; viscosity 1290 cps).

An adhesive was prepared as described in Example I using 15 parts Sol T162; 52 parts ECR 149B; 8 parts Kristalex 5140; 25 parts mineral oil and 0.2 parts antioxidant. When tested as described above, the adhesive of this example had a viscosity of 1925 cps, and gave a tensile yield value of 0.08 MPa and an ultimate tensile of 1.40 MPa. The adhesive gave a kraft/kraft peel value of greater than 24 hours however the mode of failure was a mixture of adhesive and cohesive failure. It is most desirable that the mode of failure be completely cohesive. Thus the failure mode of the adhesive with the Sol T162 was not as desirable as that for the adhesives of the invention. For use in the disposable applications of the invention, it is critical that the viscosity be in the lower ranges (i.e. the base polymer be less than about 1000 cps) for use on thinner guage substrates which are very temperature sensitive. Compare for example, the viscosity of this formulation with the viscosity of Sample 13 prepared with similar raw materials. (The viscosity of this sample was more than three times that of Sample 13).

It will be apparent that various changes and modifications may be made in the embodiments of the invention described above, without departing from the scope of the invention, as defined in the appended claims, and it is therefore intended that all matter contained in the foregoing description shall be interpreted as illustrative only and not as limitative of the invention.

We claim:

1. A hot melt adhesive composition suitable for disposable constructions consisting essentially of:
   (a) 10 to 40% by weight of a substantially radial styrene-butadiene block copolymer having a styrene content greater than 35% by weight, a modulus at 300% elongation of at least 4.5 MPa and a solution viscosity less than 1000 cps;
   (b) 20 to 65% by weight of at least one compatible tackifying resin;
   (c) 0.1 to 4% by weight stabilizer; the remainder (to 100%) comprising at least one oil diluent.

2. The adhesive of claim 1 wherein the styrene butadiene copolymer contains 37 to 40% styrene, has a modulus at 300% elongation of at least 4.6 MPa and a solution viscosity of 640 to 750 cps.

3. The adhesive of claim 1 wherein the tackifying resin is selected from the group consisting of natural and modified rosins; glycerol and pentaerythritol esters of natural and modified rosins; copolymers and terpolymers of natural terpenes; polyterpene resins having a softening point, as determined by ASTM method E28-58T, of from about 80° to 150° C.; phenolic modified terpene resins and hydrogenated derivatives thereof; aliphatic petroleum hydrocarbon resins having a Ball and Ring softening point of from about 70° to 135° C.; aromatic petroleum hydrocarbon resins and the hydrogenated derivatives thereof; and alicyclic petroleum hydrocarbon resins and the hydrogenated derivatives thereof.

4. The hot melt adhesive composition of claim 1 wherein the styrene butadiene copolymer is present in an amount of 15 to 25% by weight.

5. A disposable article comprising at least one polyethylene or polypropylene substrate bonded to at least one tissue, elastic, non-woven, polyethylene or polypropylene substrate using a hot melt adhesive composition consisting essentially of:
   (a) 10 to 40% by weight of a substantially radial styrene-butadiene bench copolymer having a styrene content greater than 35% by weight, a modulus at 300% elongation of at least 4.5 MPa and a solution viscosity less than 1000 cps;
   (b) 20 to 65% by weight of at least one compatible tackifying resin;
   (c) 0.1 to 4% by weight stabilizer; the remainder (to 100%) comprising at least one oil diluent.

6. The disposable article of claim 5 wherein the styrene butadiene wherein the styrene butadiene copolymer contains 37 to 40% styrene, has a modulus at 300% elongation of at least 4.6 and a solution viscosity of 640 to 750 cps.

7. A disposable article of the multi-line construction comprising at least one polyethylene or polypropylene substrate bonded to at least one tissue, non-woven, polyethylene or polypropylene substrate using a hot multi-adhesive composition consisting essentially of:
   (a) 10 to 40% by weight of a substantially radial styrene-butadiene bench copolymer having a styrene content greater than 35% by weight, a modulus at 300% elongation of at least 4.5 MPa and a solution viscosity less than 1000 cps;
   (b) 20 to 65% by weight of at least one compatible tackifying resin;
   (c) 0.1 to 4% by weight stabilizer; the remainder (to 100%) comprising at least one oil diluent.

8. The disposable article of claim 7 wherein the styrene butadiene copolymer contains 37 to 40% styrene, has a modulus at 300% elongation of at least 4.6 and a solution viscosity of 640 to 750 cps.

9. A method for imparting elongation resistant gathers to disposable articles wherein elastic is bonded to a polyethylene, polypropylene, tissue or non-woven substrate using a hot melt adhesive composition consisting essentially of:
   (a) 10 to 40% by weight of a substantially radial styrene-butadiene bench copolymer having a styrene content greater than 35% by weight, a modulus at 300% elongation of at least 4.5 MPa and a solution viscosity less than 1000 cps;
   (b) 20 to 65% by weight of at least one compatible tackifying resin;
   (c) 0.1 to 4% by weight stabilizer; the remainder (to 100%) comprising at least one oil diluent.

10. The disposable article of claim 9 wherein the styrene butadiene copolymer contains 37 to 40% styrene, has a modulus at 300% elongation of at least 4.6 and a solution viscosity of 640 to 750 cps.

* * * * *